United States Patent [19]
Willner et al.

[11] Patent Number: 5,897,515
[45] Date of Patent: Apr. 27, 1999

[54] ANKLE-FOOT ORTHOSIS

[75] Inventors: Stig Willner, Malmö; Karl Engdahl, Malmö Komposit, both of Sweden

[73] Assignee: Light Weight Support AB, Sweden; by said Stig Willner

[21] Appl. No.: 08/795,973

[22] Filed: Feb. 5, 1997

[51] Int. Cl.$^6$ .................................................. A61F 5/00
[52] U.S. Cl. ................................................. 602/27; 602/6
[58] Field of Search .................. 602/5–8, 23, 27–29; 264/222, 223

[56] References Cited

U.S. PATENT DOCUMENTS

| | | | |
|---|---|---|---|
| 2,847,991 | 8/1958 | Andrews | 602/28 |
| 2,949,111 | 8/1960 | Rutoistenmaki | 602/28 |
| 3,916,886 | 11/1975 | Rogers | 602/28 |
| 4,349,016 | 9/1982 | Glassman et al. | 602/23 |
| 4,489,717 | 12/1984 | Moissonnier | 602/23 X |
| 4,862,900 | 9/1989 | Hefele . | |
| 5,219,324 | 6/1993 | Hall | 602/28 |
| 5,507,720 | 4/1996 | Lampropoulos | 602/27 |
| 5,573,501 | 11/1996 | Ruscito et al. | 602/27 X |
| 5,609,568 | 3/1997 | Andrews | 602/28 |

FOREIGN PATENT DOCUMENTS

WO9104721  4/1991  WIPO .

*Primary Examiner*—Linda C. M. Dvorak
*Attorney, Agent, or Firm*—Cooper & Dunham

[57] ABSTRACT

An ankle-foot orthosis made of a carbon fiber reinforced material having low weight is carried on the front of the lower leg, extending over the lateral ankle and preventing plantar flexion. The orthosis may be worn under ordinary clothes and shoes and promotes a more natural gait pattern. The ankle-foot orthosis comprises a frame of thin flexible material extending over the front of the lower leg, anterior of the lateral ankle and beneath the sole of the foot and a supporting portion of rigid material extending over a narrow part of the front of the lower leg, anterior of the lateral ankle and beneath the part of the sole of the foot. The orthosis also comprises a fastening means for fastening the orthosis to the leg. In a preferred embodiment the orthosis comprises a substantially inflexible reinforcement element and a tough flexible element, the reinforcement element extending over a narrow part of substantially the whole frame and the flexible part extending over a substantial part of the sole of the foot. The frame is preferably made of thin flexible fiber glass reinforced plastic resin material, said reinforcement element being made of rigid carbon fiber reinforced plastic resin material. Said tough flexible element is preferably made of aramid fiber reinforced plastic resin.

15 Claims, 3 Drawing Sheets

FIG. 1
FIG. 2
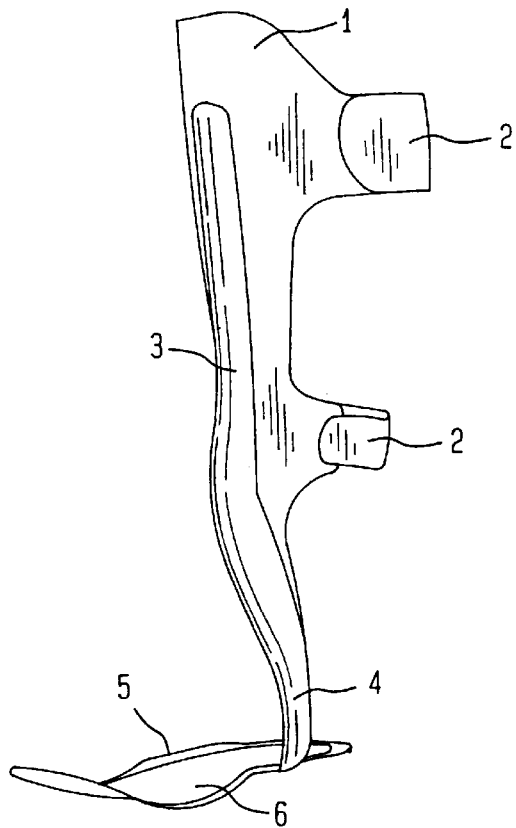
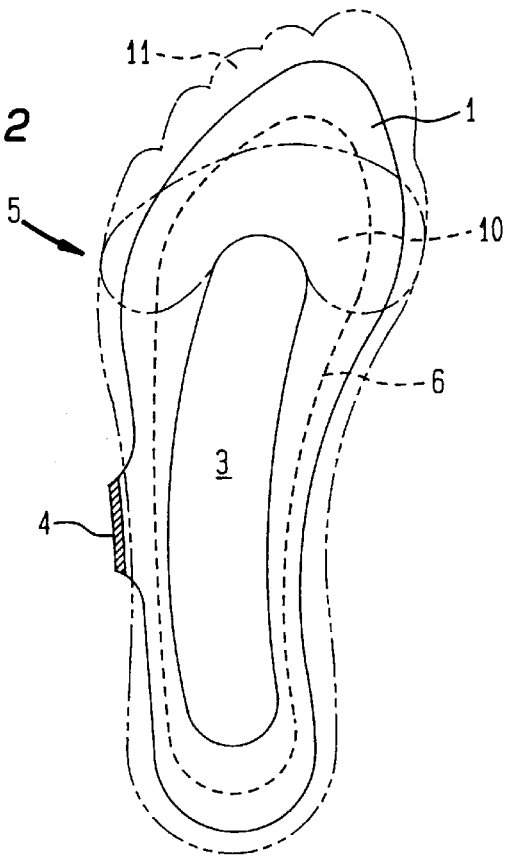

ANKLE-FOOT ORTHOSIS

RELATED APPLICATIONS

The present application is related to the International patent application filed May 15, 1995, under number PCT/SE95/00541, U.S. Ser. No. 08/737,184, now abandoned entitled PREFABRICATED ORTHOSIS OF COMPOSITE MATERIAL by the same inventors as the present application.

FIELD OF THE INVENTION

This invention relates to an ankle-foot orthosis and, more particularly, an ankle-foot orthosis made of a carbon fiber reinforced material having low weight. It is carried on the front of the lower leg, extending over the lateral ankle and preventing plantar flexion. The orthosis may be worn under ordinary clothes and shoes and promotes a more natural gait pattern.

BACKGROUND OF THE INVENTION

The prior art ankle-foot orthosis usually comprises a dorsal splint of metal or plastic extending behind the Achilles tendon and merging with a foot-plate under the sole. The orthosis is fastened by straps extending from the dorsal splint around the lower leg.

It is disadvantageous that the splint is located behind the foot and Achilles tendon since the movement of the joint is affected unfavorably producing a stiff gait. Also, the Achilles tendon and calf are often swollen and painful to touch, causing unnecessary pain to the patient and preventing a natural gait which causes heavy stresses on joints and muscles of the lower extremities and sometimes even in the back.

Further, the metal dorsal splint makes the orthosis heavy which is, of course, not comfortable when walking.

Still further, the location of the splint requires space inside the shoe and, thus, the patient's normal shoes cannot be used with the prior art orthosis.

Thus, there is a need for an improved ankle-foot orthosis having light weight and promoting a more natural gait as well as enabling use of the patient's normal clothes and shoes.

SUMMARY OF THE INVENTION

The present invention solves the above-mentioned problem by providing an ankle-foot orthosis comprising a frame of thin flexible material extending over the front of the lower leg, anterior of the lateral ankle and beneath the sole of the foot and a supporting portion of rigid material extending over a narrow part of the front of the lower leg, anterior of the lateral ankle and beneath the part of the sole of the foot. The orthosis also comprises a fastening means for fastening the orthosis to the leg.

It is preferred that the orthosis comprises a substantially inflexible reinforcement element and a tough flexible element, the reinforcement element extending over a narrow part of substantially the whole frame and the flexible part extending over a substantial part of the sole of the foot.

The frame is preferably made of thin flexible fiber glass reinforced plastic resin material, said reinforcement element being made of rigid carbon fiber reinforced plastic resin material. Said flexible element is preferably made of aramid fiber reinforced plastic resin.

It is an advantage of the present invention that the orthosis is thin and light-weight, enabling use of normal clothes and shoes.

It is a further advantage that the supporting portion extends over the front of the leg and anterior of the lateral ankle enabling the orthosis to take the impact when the heel is put down and support the movement in the toe-off stage to obtain a more normal gait.

Other objects, advantages and novel features of the present invention will become apparent from the following detailed description of the invention when considered in conjunction with the accompanying drawings.

BRIEF DESCRIPTION OF THE DRAWINGS

FIG. 1 is a perspective view of an ankle-foot orthosis according to the present invention;

FIG. 2 is a cutaway top view of a foot plate of the orthosis of the invention, the contour of a foot being outlined in phantom lines;

DETAILED DESCRIPTION OF THE PREFERRED EMBODIMENTS

Figure 3:
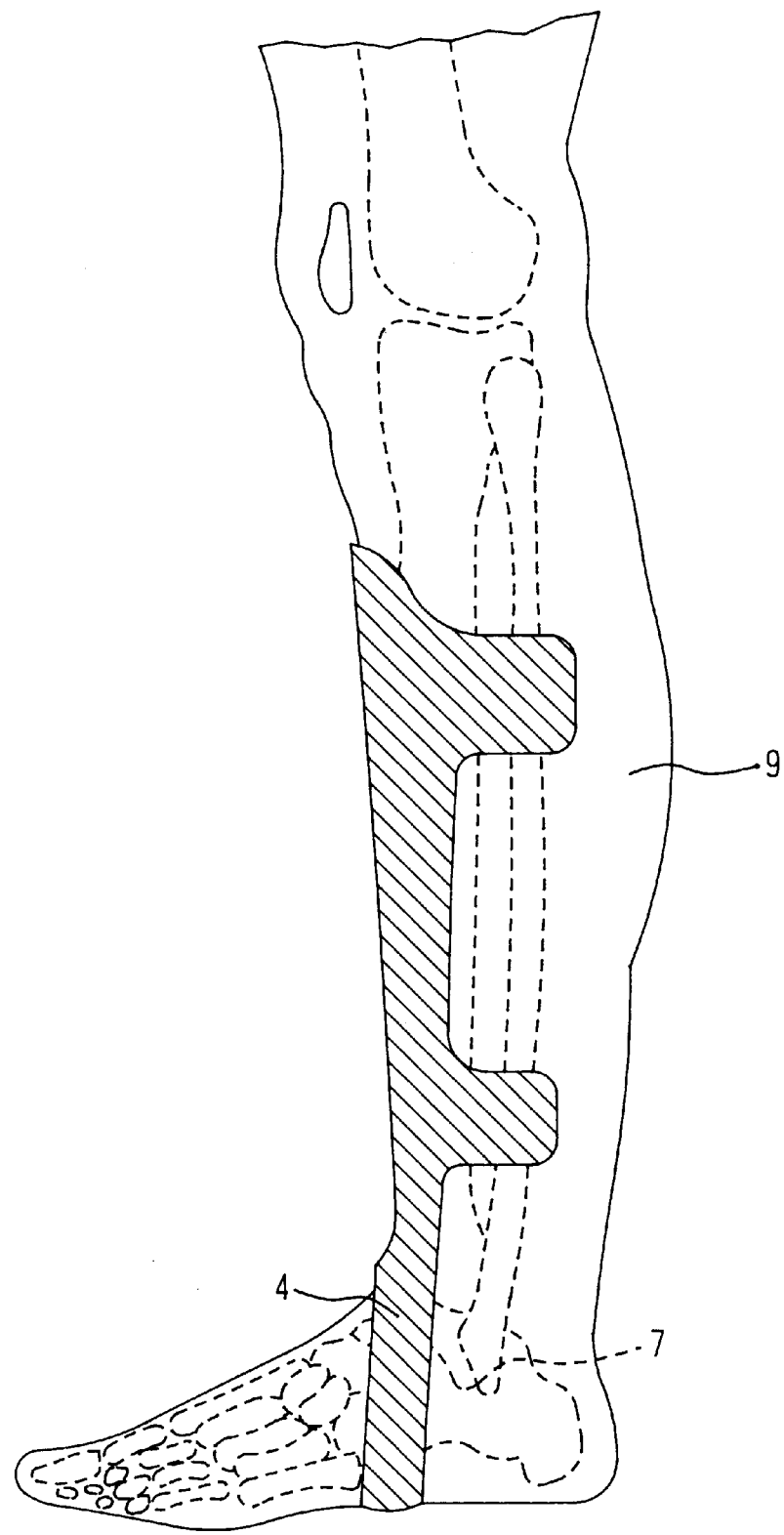
FIG. 3 is a side view of the orthosis placed on the lower leg of a patient.

An ankle-foot orthosis according to the present invention is shown in FIG. 1. An orthosis for the left foot is shown while it should be understood that a mirror image of the orthosis should be used for the right foot. The orthosis comprises a frame 1 of composite material and straps 2 for securing the orthosis to the lower leg. The straps and orthosis are provided with so-called Velcro or hook-and-loop type surfaces providing an easy means of taking on and off the orthosis.

In the frame 1 a reinforcement element 3 is embedded. The reinforcement element extends over a narrow part of the leg portion of the frame on the front of the lower leg. The reinforcement element 3 continues by way of a brace portion 4 to a foot plate 5 in which the reinforcement element again is embedded as a narrow portion. As is best shown in FIG. 2, the foot plate 5 also comprises another embedded element, viz. a tough flexible element 6. The reinforcement element 3 and the tough element 6 together provide the supporting portion of the orthosis.

Except where the reinforcement element is embedded in the frame 1, the frame 1 is flexible. This means that the orthosis can accomodate thick and thin legs by tightening or loosing the straps. Also, the frame 1 may be cut by an ordinary pair of scissors to adjust the height of the orthosis and width of the foot-plate 5 as is described more in detail below.

In order for a prefabricated orthosis to be useful, it must fulfil certain requirements. As is mentioned above, it is flexible in certain areas, making the orthosis easy to take off and put on and making it suitable for extremities having different sizes, and furthermore requiring only a few sizes to fit the majority of the population. It must be rigid in other areas so as to give an adequate immobilisation of the ankle joint and of lower part of the lower extremities, etc. and it should furthermore have a low weight as well as a surface which is well tolerated both on the inside and the outside.

The frame 1 is made from a thin yarn fabric of fiberglass which is pre-impregnated with an epoxy matrix into a prepreg. A double inner and outer layer is suitable for an ankle-foot orthosis. For certain orthoses a smaller number of layers may be suitable at the edges of the orthosis to make it more flexible. Each finished layer has a thickness of at least about 0.2 mm.

Between the fiber-glass layers, the two-part reinforcement element 3 is placed. Where the reinforcement element is to be strongest, e.g. at the brace portion 4, it consists of a carbon fiber fabric impregnated with an epoxy matrix into a prepreg. A number of layers as necessary is used to obtain the suitable strength. In the upper portion of the reinforcement element (at 3 in FIG. 1), the carbon fibers are conveniently arranged longitudinally to provide a great bending resistance but lesser torsion resistance. The directions of the carbon fibers in the various layers of the brace portion 4 are preferably arranged in a crisscross manner as well as longitudinally to obtain the greatest possible bending and torsion resistance. In the foot plate portion of the reinforcement element, the carbon fibers are conveniently arranged in a crisscross manner to provide a great torsion resistance but lesser bending resistance. The cured carbon fiber material has a coefficient of elasticity comparable to that of steel. Each finished layer has a thickness of at least about 0.3 mm. The width of the reinforcement element ranges from 25 to 40 mm depending on the size of the orthosis.

The forming of the prepregs is made on a tool shaped in accordance with a cast of the desired extremity part, in this case the lower leg and the foot, of suitable size. The material is cured in an oven in 120° C. for 120 minutes. After this, the material may be surface treated, e.g. painted in any wanted colour, and the padding and the Velcro fasteners may be applied. It is also possible to use a colored epoxy matrix in which case additional painting of the orthosis will not be necessary.

When using the orthosis, the frame 1 expands if the patient has thick legs whereas it can be pulled together by the Velcro strap fasteners if the patient has thin legs. At the same time, the reinforcement element 3 remains almost completely immobile.

Furthermore, the frame of fiber glass reinforcement plastic resin is not very hard and may be cut by an ordinary pair of scissors. Thus, the height of the orthosis may be adjusted by cutting off a portion at the top edge 8 if the patient has relatively short legs. Also, the width of the foot-plate 5 may be adjusted by cutting along the edges thereof in order to accomodate the foot-plate 5 inside a shoe. The orthosis of the invention is intended for use inside the patient's normal shoes and this is possible since only the brace portion 4 needs some extra space where it is protruding from the shoe, see especially FIG. 2. The patient should use ordinary socks with the orthosis. If necessary, an inner sole of a shoe may be removed for better comfort.

As is seen in FIG. 2, the foot-plate 5 comprises three portions having different strength and flexibility. In the central part and extending longitudinally of the footplate the reinforcement element 3 is embedded as mentioned previously. Surrounding the reinforcement element 3 on the foot-plate 5 is a further element 6 having great toughness and flexibility. The flexible element 6 is made of a double layer of aramid fibers (such as sold under the trademark Kevlar) preimpregnated with an epoxy matrix into the prepreg. The epoxy matrix is the same in all the different materials of the orthosis. Of course, the various layers have to be formed at the same time. The peripheral portion of the foot-plate only comprises the fiber glass reinforced layer constituting the frame 1. This peripheral portion may be cut off completely, if necessary, for the reasons stated above.

The ball 10 of the foot 11 is also outlined in FIG. 2 by dotted lines. As may be seen, the ball of the foot should be located in front of the reinforcement element 3 but supported by the flexible element 6. This enables bending upwards of the toes when walking as is described in further detail below with reference to the gait pattern analysis of FIG. 4.

As is shown in FIG. 3 the orthosis is carried on the lower leg 9. In FIG. 3, the lower leg is outlined together with the skeleton bones in phantom lines. It may be seen that the brace portion 4 runs anterior or in front of the lateral foot joint 7 resulting in a natural gait pattern and other advantages as is outlined below. In FIG. 3 the straps 2 are not shown for better clarity.

The orthosis is produced in three sizes in order to fit the majority of the grown-up population, both male and female. The small size of the orthosis takes shoe-sizes up to 10 (Europe up to 38), medium: shoe-size 10–11 (Europe 38–42) and large: shoe-size 11–12 (Europe 42–45).

The orthosis is suitable for use at the following indications. The patient has neurological disorders, e.g. weakness of the peroneal nerve, with muscular weakness in the lower extremities, especially the foot, resulting in ankle instability. A typical example is drop foot. The disorder may be the result of disease, tumors, infection, radiation treatment, and accidents etc. Contraindications are e.g. severe spasticity, ankle edema and diabetes with ulcers.

As is mentioned previously, the object of the anklefoot orthosis of the invention is to achieve a more natural and dynamic gait. A normal gait pattern has been aimed at and was used as a basis in developing the orthosis. The orthosis also assists in coordinating the foot movement by keeping the structures of the foot in a functional position.

Figure 4:
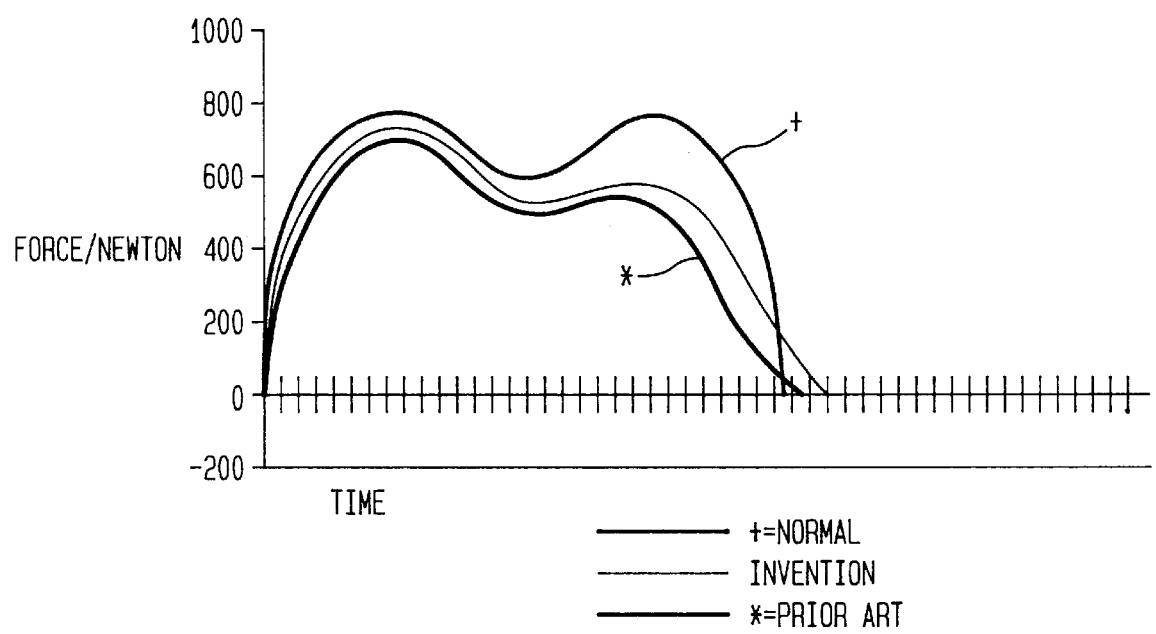
FIG. 4 is a gait diagram of an analysis of the gait cycle using orthoses in accordance with the prior art and the present invention.

A gait cycle analysis using the orthosis of the invention is shown in FIG. 4. The lower curve is for a prior art orthosis, the intermediate curve for an orthosis according to the present invention, and the top curve for a normal healthy person. The force is measured by a foot plate on the floor, that is the vertical force exerted by a person walking. At the heal strike the body weight is transferred through the front part of the orthosis. This is the left-hand peak of the curves. This force is eventually absorbed substantially in the soft tissue of the large calf muscle M. Gastrocnemius. The elasticity of the flexible portion 6 of the foot-plate allows a gradual plantar flexion of the foot in dependence of the body weight, the motion velocity and the position of the lower leg relative to the ground. From the supporting phase to the toe-off phase the orthosis protects the foot from inversion and eversion by bridging the ankle joint. The toe-off phase is represented by the right-hand peak of the curves. As is seen from FIG. 4, the patient using the prior art orthosis cannot obtain the necessary force during toe-off, but the patient using the orthosis of the present invention obtains an increased force. Of course, this increased forced does not act on the weak foot but on the leg where the orthosis is carried. In fact, the springing action of the foot-plate will assist the patient to move forward. The flexibility of the foot-plate will also promote a more natural gait.

Thus, it will be seen that the ankle-foot orthosis according to the invention has various advantages. The orthosis is of an extremely low weight, approximately 110 grams for the medium size, which is very important for patients having weaknesses in the leg muscles. The orthosis is very thin enabling use of normal shoes and even boots. The elasticity of the foot-plate promotes a more natural gait reducing the stresses on the front part of the foot. The orthosis stabilizes the ankle joint to prevent a distortion tendency. The orthosis may be individually adjusted by cutting or grinding the edges of the foot-plate or other edges of the fiber glass reinforced plastic.

Furthermore, the orthosis is primarily in contact with the front part of the lower leg avoiding contact with sensitive areas such as the Achilles tendon, the heel and malleoli which often are subject to swelling and are sensitive to touch. It is a fact that the width of the ankle and the size of the heel bone varies over a wide range as seen for a normal healthy population. Thus, it is an advantage that the orthosis of the invention does not cover these portions of the foot-ankle joint but extends over the lateral ankle only. The orthosis is simple to put on and take off; only two straps are securing the orthosis against the leg. The orthosis is put on by first placing the foot-plate in the shoe. Thereafter the shoe is put on with the orthosis in place. If pressure points and sharp edges are experienced, these may be eliminated by applying a soft padding on the inside of the orthosis.

While the present invention has been described with reference to a specific embodiment, the description is illustrative of the invention and is not to be construed as limiting the invention. Various modifications may occur to those skilled in the art without departing from the true spirit and scope of the invention as defined by the appended claims.

We claim:

1. An ankle-foot orthosis comprising:
   a frame of thin flexible material sized and shaped to extend over the front of the lower leg, anterior of the lateral ankle on one side of the ankle only and beneath the sole of the foot;
   a supporting portion sized and shaped to extend over a narrow part of the front of the lower leg, anterior of the lateral ankle on one side of the ankle only and beneath only a part of the sole of the foot, the supporting portion comprising a substantially inflexible reinforcement element sized and shaped to extend behind the ball of the foot; and
   a fastening means for fastening the orthosis around the leg.

2. An ankle-foot orthosis according to claim 1, wherein the supporting portion further comprises a tough flexible element.

3. An ankle-foot orthosis according to claim 2, wherein the flexible element is sized and shaped to extend over a substantial part of the sole of the foot including the ball of the foot.

4. An ankle-foot orthosis according to claims 2 or 3, wherein said reinforcement element is made of carbon fiber reinforced plastic resin and said flexible element is made of aramid fiber reinforced plastic resin.

5. An ankle-foot orthosis comprising:
   a frame of thin flexible fiber-glass reinforced plastic resin material sized and shaped to extend over the front of the lower leg, anterior of the lateral ankle and on one side of the ankle only and beneath the sole of the foot;
   a reinforcement element of rigid carbon fiber reinforced plastic resin material sized and shaped to extend over a narrow part of the front of the lower leg, anterior of the lateral ankle on one side of the ankle only and beneath a narrow part of the sole of the foot behind the ball of the foot; and
   a fastening means for fastening the orthosis around the leg.

6. An ankle-foot orthosis according to claim 5, further comprising a tough flexible element made of aramid fiber reinforced plastic resin in the portion of the orthosis sized and shaped to extend over a substantial part of the sole of the foot supporting the ball of the foot.

7. An ankle-foot orthosis according to claims 5 or 6, wherein the fiber-glass reinforced plastic comprises a number of layers of yarn fabric impregnated with an epoxy matrix.

8. An ankle-foot orthosis according to claim 7, wherein each fiber-glass reinforced layer is $\leq 0.2$ mm thick.

9. An ankle-foot orthosis according to claim 8, comprising two fiber-glass reinforced layers.

10. An ankle-foot orthosis according to claim 5 or 6, wherein the carbon fiber reinforced plastic comprises a number of layers of single-direction carbon fiber fabric impregnated with an epoxy matrix.

11. An ankle-foot orthosis according to claim 10, wherein each carbon fiber reinforced layer is arranged at an angle to other layers.

12. An ankle-foot orthosis according to claim 10, wherein the fiber-glass reinforced plastic comprises of a number of layers of yarn fabric impregnated with an epoxy matrix each carbon fiber reinforced layer is $\leq 0.3$ mm thick.

13. An ankle-foot orthosis according to claim 11, wherein each carbon fiber reinforced layer is $\leq 0.3$ mm thick.

14. An ankle-foot orthosis according to claim 12, comprising one to four carbon fiber reinforced layers.

15. An ankle-foot orthosis according to claim 13, comprising two to four carbon fiber reinforced layers.

* * * * *